(12) United States Patent
Türck et al.

(10) Patent No.: US 6,184,220 B1
(45) Date of Patent: Feb. 6, 2001

(54) ORAL SUSPENSION OF PHARMACEUTICAL SUBSTANCE

(75) Inventors: Dietrich Türck, Ulm; Veit Schmelmer, Biberach, both of (DE)

(73) Assignee: Boehringer Ingelheim Pharma KG, Ingelheim (DE)

(*) Notice: Under 35 U.S.C. 154(b), the term of this patent shall be extended for 0 days.

(21) Appl. No.: 09/276,208

(22) Filed: Mar. 25, 1999

Related U.S. Application Data

(60) Provisional application No. 60/084,498, filed on May 6, 1998.

(30) Foreign Application Priority Data

Mar. 27, 1998 (EP) .................................... 98105568

(51) Int. Cl.⁷ .............................. A61K 31/54; A61K 9/10
(52) U.S. Cl. ...................... 514/226.5; 424/494; 514/937; 514/970; 514/974
(58) Field of Search ................. 514/226.5, 937, 514/970, 974, 225.2, 225.8; 424/489, 494

(56) References Cited

U.S. PATENT DOCUMENTS 4,835,187    5/1989  Reuter et al. .
5,085,868  * 2/1992  Mattsson et al. ..................... 424/490
5,460,828  * 10/1995 Santus et al. ........................ 424/489
5,552,160  * 9/1996  Liversidge et al. .................. 424/489
5,559,535  * 9/1996  Otsuka et al. ......................... 347/14
5,674,888  * 10/1997 Polansky et al. ..................... 514/418
6,063,783  * 5/2000  Pineiro et al. ....................... 514/248

FOREIGN PATENT DOCUMENTS 0179430      4/1986  (EP) .
560329 A1  * 9/1993  (EP) .
WO 98/17250   4/1998  (WO) .

* cited by examiner

Primary Examiner—Robert H. Harrison
(74) Attorney, Agent, or Firm—Robert P. Raymond; Mary-Ellen M. Devlin; Timothy X. Witkowski

(57) ABSTRACT

The present invention relates to orally administered suspensions of pharmaceutical active substances of the NSAID type, particularly the antirheumatic agent Meloxicam, which are stabilized by the addition of small amounts of highly dispersed silicon dioxide using high shear forces and adding small amounts of hydrophilic polymers to form a three-dimensional siloid structure, and a process for the preparation thereof.

13 Claims, 1 Drawing Sheet

ORAL SUSPENSION OF PHARMACEUTICAL SUBSTANCE

This application is a continuation-in-part of prior provisional application Ser. No. 60/084,498, filed May 6, 1998.

BACKGROUND OF THE INVENTION

The present invention relates to orally administered suspensions of pharmaceutically active substances of the NSAID type (nonsteroidal-antiinflammatory drugs), but particularly the antirheumatic agent meloxicam and a process for preparing them.

Various pharmaceutical forms are used for oral administration of drugs. Thus, in addition to solid single-dose forms such as tablets, hard and soft gelatin capsules, liquid forms such as solutions and syrups are also given, in which the dose to be administered can be adjusted by means of the volume given.

Solutions and syrups have the advantage that they can be taken easily and safely even by patients who have trouble taking solid, single-dose forms (e.g. children and older patients). Liquid preparations are advantageously easy to measure out for veterinary use.

However, it should be borne in mind that even with the same dosage and the same method of administration, the activity of the same pharmaceutical substance may vary. These variations mean that the therapeutic effect clinically demonstrated for a drug in a specific preparation cannot be achieved with a different preparation of the same drug, and furthermore within a course of treatment one preparation cannot readily be exchanged for another. Preparations which are not therapeutically equivalent are known as "non-bioequivalent".For the oral administration of pharmaceutical preparations, the drug is usually absorbed faster from liquid preparations, particularly solutions, than from tablets or capsules and these drugs are consequently not always bioequivalent (Bauer K. H.; Frömming K. -H.; Führer C., Pharmazeutische Technologie, $5^{th}$ Edition 1997, Gustav Fischer Verlag, Stuttgart, page 213).

Meloxicam is an antirheumatic agent belonging to the NSAID's. NSAID's are cyclooxygenase inhibitors, whilst meloxicam has been shown to have a selective inhibitory effect on the isoenzyme COX-2 and consequently a reduced risk of undesirable gastrointestinal side effects. For safe administration of meloxicam and other active substances, e.g. other NSAID's, a liquid oral preparation is desirable as an alternative to the solid form (capsule, tablet), particularly in pediatrics and in veterinary use.

The complex objective of the present invention was primarily to produce an orally administered liquid preparation of meloxicam. The formulation should take effect rapidly when first used in acute cases. However, the substance is preferably used for long-term therapy. In such long-term therapy, the liquid oral formulation should be bioequivalent to other oral formulations (tablet, capsule) in the steady state in order to allow therapy with either a liquid or solid oral formulation as desired. At the same time, the liquid preparation should have a pleasant flavor in order to be acceptable to children and thus ensure that it is taken as specified and the treatment is ensured. In addition, the liquid preparation should preferably not contain any ethanol, since the possibility of ethanol having a harmful effect even in physiologically acceptable, non-toxic concentrations cannot be ruled out completely, particularly in children. Moreover, when ethanol is used, there is the risk of abuse by alcohol-dependent patients or relapse on the part of formerly alcohol-dependent patients. The suitability of the formulation for diabetic patients should also be taken into account. To ensure exact dosage of a liquid oral preparation of meloxicam, the preparation should also be homogeneous over a sufficient length of time during its removal from the primary packaging.

In addition, the preparation should also be suitable for use in animals. The veterinary formulation should also have a smell and flavor which are suitable for numerous types of animals which can be treated with antirheumatic drugs, particularly various species of mammals, to ensure that the course of treatment is completed and the therapy is guaranteed, on the basis of good acceptance.

One obvious way of preparing a liquid oral formulation of a pharmaceutically active substance is to dissolve the substance in physiologically inert solvents (especially pharmaceutical grade water). However, this approach is unsuitable in many cases. To ensure the desired pleasant taste of a liquid oral formulation, e.g. meloxicam, it is not possible to use solutions, since the substance in the dissolved state has an unpleasant taste of its own. This taste is apparent in all the solvents which can be used for the oral administration of solutions and cannot be adequately masked even by the addition of flavor correcting agents such as flavorings and sweeteners.

However, meloxicam does not have a noticeable flavor of its own when the substance is suspended in a physiologically inert dispersion medium for a liquid oral preparation and the solubility of meloxicam in the dispersion medium used is very slight. This provided a suitable approach to solving the problem. This approach can be applied analogously to other active substances of the NSAID category. Since a clearly noticeable unpleasant taste is present even at a concentration of over 500 $\mu$g/ml of dissolved meloxicam, the solubility of this active substance in the dispersion media used must be below this threshold.

When a suspension of active substance is used there is the problem that the homogeneity of the suspension has to be ensured for a sufficient length of time during removal from the primary packaging (e.g. glass bottle, 100 ml) to ensure accurate dosing. However, the sedimentation of solids dispersed in liquid media cannot be prevented but only delayed for a greater or lesser period. One conventional approach to delaying sedimentation is, for example, by increasing the viscosity of the dispersing medium by the addition of suitable substances, e.g. organic hydrocolloid forming agents, e.g. cellulose ether, or silicon dioxide as a thickener. Increasing the viscosity of the dispersing agent does, however, have the serious disadvantage that it makes it considerably more difficult to redisperse the sediment formed, to the extent that if the suspension is too viscous it is impossible to reconstitute the suspension at all. Moreover, the caking caused by contact of the individual particles under the effects of gravity during storage of the suspension must be avoided. It is known from the literature to prevent caking by, for example, controlled flocculation of such systems by the adsorption of potential-determining ions (Sucker H., Fuchs P., Speiser P., Pharmazeutische Technologie, $5^{th}$ Edition 1991, Georg Thieme Verlag, Stuttgart, p. 423). The industrial manufacture of stable suspensions by controlled flocculation is subject to limitations, since it is difficult to reproduce the optimum properties of suspension systems of this kind owing to the variability of the suspended solid and the stability of the suspension is considerably affected by the adjuvants used.

BRIEF SUMMARY OF THE INVENTION

Surprisingly, the suspension of a pharmaceutically active substance of the NSAID type can be stabilised by the addition of small amounts of highly dispersed silicone dioxide in the presence of small amounts of hydrophilic polymers. Because of the low concentration of highly dispersed silicon dioxide and hydrophilic polymer in the dispersion medium, the viscosity is low; unwanted increased in viscosity, which will prevent reconstitution of the suspension, caused by gel-like thickening of the dispersion medium does not occur if at the same time small amounts of hydrophilic polymer which are soluble in the dispersion medium are added to the medium and the silicon dioxide is added to the suspension with the aid of high shear forces. Suitably high shear forces can be produced with a suitable shear-intensive homogenising mixer, e.g. with mixers of the series "Becomix" made by Messrs. A. Berents GmbH & Co. KG, Henleinstr. 19, D-28816 Stuhr, which comprise rapidly rotating homogenizers working on the rotor-stator principle. A circumferential rotor speed of about 25 to 27 m/s is particularly suitable for generating sufficiently high shear forces and is used to introduce the highly dispersed silicon dioxide into the dispersing agent for about 10–15 minutes, e.g. using the mixers Becomix RW 15/RW 60/RW 1000. This produces a special siloid structure which consists of a spongy three-dimensional structure of hydratised highly dispersed silicon dioxide shot through with cavities, the active substance being adsorbed onto said structure.

Suitable highly dispersed silicon dioxide has a specific surface area of at least 50 m$^2$/g, preferably 100 to 400 m$^2$/g, for example, whilst a specific surface area of about 200 m$^2$/g is particularly preferred (e.g. Aerosil® 200).

DETAILED DESCRIPTION OF THE INVENTION

Figure 1:
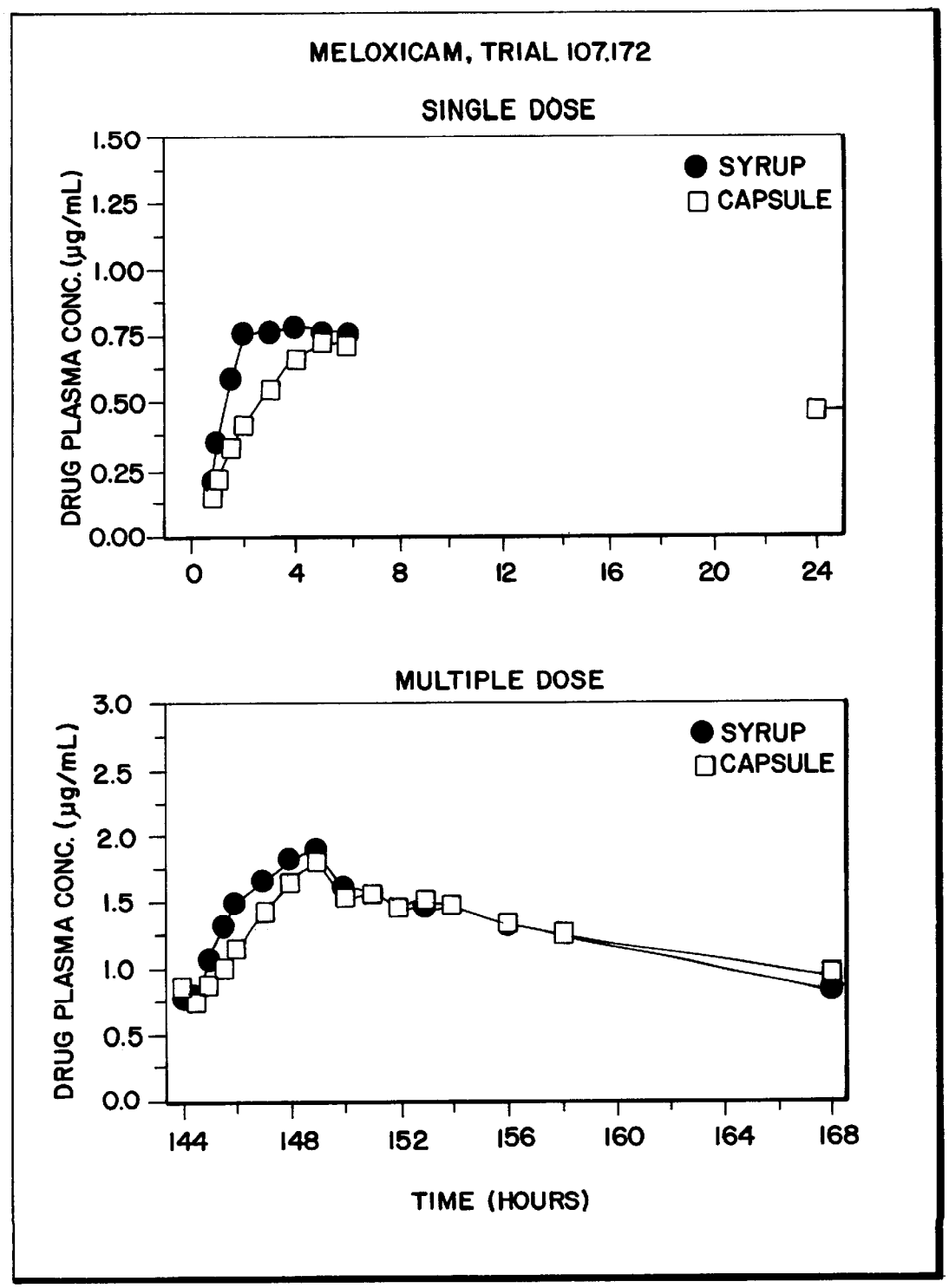
FIG. 1 shows two graphs displaying plasma levels of meloxicam after oral administration of the suspension of the present invention and meloxicam administered in a capsule dose.

The invention relates to a suspension of a pharmaceutically active substance of the NSAID type with a suspendable particle size spectrum in a physiologically inert dispersion medium in which the active substance has very little solubility, so that the suspension has no perceptible taste of its own, for oral administration, characterised in that the suspension contains a small amount of highly dispersed silicon dioxide for stabilisation by forming a three-dimensional siloid structure, the three-dimensional siloid structure being produced by adding the silicon dioxide to the dispersion medium under the action of high shear forces, and the suspension additionally contains a small amount of hydrophilic polymer which is soluble in the dispersion medium.

The above-mentioned three-dimensional siloid structure consists of crosslinked, swollen and coherent strands of SiO$_2$ between which can be found fairly large cavities filled with dispersion medium. The suspended solid particles of the active substance, e.g. meloxicam, are adsorbed almost exclusively onto the SiO$_2$ strands. In this way, the suspended particles are rapidly and fully wetted and agglomeration of the particles of pharmaceutical substance can be prevented entirely. This results in a suspension of the active substance of exceptional homogeneity and dosing precision. The siloid structure described does not lead to any gel-like thickening of the dispersion medium but rather produces a low viscosity pourable suspension.

At the same time, the three-dimensional siloid structure acts as a sedimentation stabiliser. The structure described is very bulky and is compressed only slightly and very slowly even by sedimentation. Thus, even after months of storage, the volume of the siloid structure decreases by only about 20%. The reduction in volume caused by sedimentation does not result in undesirable caking; the sediment can be easily and quickly redispersed by the use of extremely slight mechanical forces (e.g. very gentle shaking of an oral suspension of meloxicam packaged in standard commercial glass bottles). The slowness of sedimentation ensures that the user has sufficient time to take homogeneous single doses of the oral suspension of a pharmaceutically active substance according to the invention out of its primary packaging, thus ensuring accuracy of dosing.

For example, an active substance suspension according to the invention contains 0.1–5 wt. % of highly dispersed silicon dioxide (e.g. Aerosil® 200), preferably 0.5–2 wt. %, more particularly 0.5–1.5 wt. %.

Suitable soluble hydrophilic polymers are pharmaceutical grade cellulose ethers such as hydroxyethyl cellulose (HEC), hydroxypropyl cellulose (HPC) and hydroxypropylmethyl cellulose (HPMC). Hydroxyethyl cellulose is preferred. For example, a suspension of active substance according to the invention contains 0.05–2 wt. % of water soluble cellulose ether, preferably 0.05–0.5 wt. %, but more particularly 0.05–0.1 wt. %.

Most preferably, the active substance suspension according to the invention contains 0.5–1.5 wt. % of highly dispersed silicon dioxide and 0.05–0.1 wt. % of hydroxyethyl cellulose.

The properties of a liquid oral suspension of active substance according to the invention are greatly influenced by the particle size of the suspended active substance. To achieve the rapid onset of activity which is desirable when the preparation is taken once, a small particle size is essential, ensuring the fastest possible dissolution of the active substance in gastrointestinal tract. In the particle size spectrum of the active substance which is suitable for a suspension according to the invention, therefore, at least 90% of the particles are smaller than 50 μm, preferably at least 50% of the particles are smaller than 10 μm, and most preferably about 90% of the particles are smaller than 10 μm (determined for example by laser diffractometry). A correspondingly finely dispersed grade of pharmaceutical can easily be achieved by suitably grinding a coarser grade. Suitable mills for grinding operations of this kind are the standard commercial jet mills, for example.

The small particle size of the active substance in a suspension according to the invention as described also have the advantage of a slow rate of sedimentation of the suspended particles, which favorably affects the homogeneity of the liquid oral formulation of the active substance described and correspondingly ensures a high degree of accuracy in measuring the dose.

The solubility of the active substance in suitable physiologically acceptable dispersion media should be less than 500 μg/ml. Preferably, the solubility is not more than 50 μg/ml, most preferably the solubility is not more than 5 μg/ml, but more particularly not more than 0.5 μg/ml.

It is readily possible for the skilled person to find, for any given active substance of the NSAID type, a suitable physiologically acceptable dispersion medium in which the active substance has the solubility characteristics mentioned above. For meloxicam, the physiologically acceptable dispersion medium preferably consists of an aqueous buffer system with a pH in the range from 2–4.

An orally administered suspension according to the invention may contain one or more NSAID's as pharmaceutically active substance. The classic active substance acetylsalicylic acid and the active substances of the following categories are mentioned as examples of NSAID'S:
(1) propionic acid derivatives,
(2) acetic acid derivatives,
(3) fenamic acid derivatives,
(4) biphenylcarboxylic acid derivatives,
(5) acid enolcarboxamides,
(6) diaryl heterocycles with methylsulphonyl or aminosulphonyl substituents and
(7) acid sulphonamides.

The following active substances are mentioned as examples of propionic acid derivatives, although this list should not be regarded as limiting this category of active substance:

ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid and fluprofen or the pharmaceutically acceptable salts thereof.

Examples of acetic acid derivatives include the following active substances, although the list does not constitute any restriction of this category of active substance:

indomethacin, sulindac, tolmetin, zomepirac, nabumetone, diclofenac, fenclofenac, alclofenac, bromfenac, ibufenac, aceclofenac, acemetacin, fentiazac, clidanac, etodolac and oxpinac or the pharmaceutically acceptable salts thereof.

The following active substances are mentioned as examples of fenamic acid derivatives, although the list does not constitute a limitation to this category of active substance:

mefenamic acid, meclofenamic acid, flufenamic acid, nifluminic acid and tolfenamic acid or the pharmaceutically acceptable salts thereof.

Examples of biphenylcarboxylic acid derivatives include the following active substances, although the list does not constitute a limitation of this category of active substance:

diflunisal and flufenisal or the pharmaceutically acceptable salts thereof.

The following are examples of acid enolcarboxamides (oxicams), although the list does not constitute a restriction to this category of active substance:

piroxicam, tenoxicam, lornoxicam and meloxicam or the pharmaceutically acceptable salts thereof.

Nimesulide is mentioned by way of example of an acid sulphonamide, but should not constitute a restriction to this category of active substances.

Chemical structures, pharmacological activity, side effects and information regarding the usual dosage ranges for the above-mentioned NSAID's are given for example in Physician's Desk Reference, 35$^{th}$ Edition, 1981; The Merck Index, 12$^{th}$ Edition, Merck and Company, Rahway, N.J. (1996); Cutting's Handbook of Pharmacology, 6$^{th}$ Edition, Ed. T. Z. Czacky, M.D., Appleton-Century-Crofts, New York, 1979, Chapter 49:538–550.

A dosage unit for the following NSAID's may be, for example:

100–500 mg Diflunisal, 25–100 mg Zomepirac sodium, 50–400 mg Ibuprofen, 125–500 mg Naproxen, 25–100 mg Flurbiprofen, 50–100 mg Fenoprofen, 10–20 mg Piroxicam, 5–20 mg Meloxicam, 125–250 mg Mefenamic acid, 100–400 mg Fenbufen and 25–50 mg Ketoprofen.

Particularly preferred oral administered suspensions according to the invention are those which contain as active substance an acid enolcarboxamide, especially meloxicam.

Meloxicam is an NSAID with the structural type of an enolic acid and exhibits a distinctly pH-dependent solubility. The minimum solubility in buffered aqueous systems is found at pH values from 2–4. The solubility in this pH range is less than 0.5 $\mu$g/ml (Luger P., Daneck K., Engel W., Trummlitz G., Wagner K., Structure and physicochemical properties of meloxicam, a new NSAID, Eur. J. Pharm. Sci. 4 (1996), 175–187).

Suitable dispersion media for a liquid oral suspension of meloxicam according to the invention are therefore physiologically acceptable aqueous buffer systems with a pH in the range from 2–4, mixtures thereof or mixtures thereof with other physiologically acceptable liquids which are additionally suitable for improving specific properties of the meloxicam suspension, especially for adjusting the viscosity of the dispersion medium in order to reduce the rate of sedimentation of the suspended particles of pharmaceutical, to ensure that the liquid oral preparation has a pleasant flavor and to improve the wetting qualities of the suspended pharmaceutical particles.

Other physiologically acceptable liquids in the sense of the invention described are preferably glycerol and optionally aqueous solutions of sugar alcohols such as sorbitol, mannitol and xylitol, and mixtures thereof. In a suspension according to the invention these substances have the advantage of increasing the viscosity of the dispersion medium and hence reducing the rate of sedimentation of the suspended pharmaceutical particles and making it easier to handle when the liquid formulation is transferred into metering aids (e.g. standard measuring spoons or special metering systems such as metering syringes) and when the liquid formulation is measured out in drops (e.g. standard dropper inserts), of their slightly sweet inherent flavor which gives the liquid oral formulation a pleasant taste, of their suitability for diabetic patients and animals which can be treated with antirheumatic drugs and of improving the wetting properties of the suspended pharmaceutical particles.

Suitable physiologically acceptable aqueous buffer systems with a pH in the range from 2–4 include, for example, sodium dihydrogen-phosphate dihydrate/citric acid monohydrate buffer, glycine/HCl (S. P. Sørensen, Biochem. Z., 21, 131 (1909); Biochem. Z., 22, 352 (1909)), Nacitrate/HCl (S. P. Sørensen, Biochem. Z., 21, 131 (1909); Biochem. Z., 22, 352 (1909)), K-hydrogen phthalate/HCl (Clark and Lubs, J. Bact., 2, 1 (1917)), citric acid/phosphate (T. C. McIlvaine, J. Biol. Chem., 49, 183 (1921)), citrate-phosphate-borate/HCl (Teorell and Stenhagen, Biochem. Z., 299, 416 (1938)) and Britton-Robinson Buffer (Britton and Welford, J. Chem. Soc., 1, 1848 (1937)).

Preferably, a dispersion medium for a liquid oral suspension of meloxicam according to the invention is based on an aqueous buffer system with a pH in the range from 2–4 mixed with one or more of the physiologically acceptable liquids glycerol and aqueous solutions of the sugar alcohols mannitol, sorbitol and xylitol.

For example, the dispersion medium of a liquid oral suspension of meloxicam according to the invention consists of mixtures of about 30–50% aqueous buffer system, pH 2–4, preferably aqueous sodium dihydrogen phosphate dihydrate/citric acid monohydrate buffer, about 10–20% glycerol, about 10–20% xylitol and about 20–30% sorbitol or mannitol solution (70% sorbitol or mannitol in water). Glycerol and the above-mentioned sugar alcohols may be present either individually or in admixture with one another in the dispersion medium.

The suspension ready for use may contain varying amounts of the active substance meloxicam, e.g. 0.050 to 3.000 g/118 g, preferably 0.050 to 2.000 g/118 g, but particularly 0.050 to 1.5 g/118 g, based on the mass of the preparation ready for use.

To improve the flavor still further, one or more flavorings and/or one or more sweeteners may be added to a liquid oral suspension according to the invention.

Suitable flavorings include, for example, liquid and powdered, water soluble natural and nature-identical flavorings. Particularly preferred are liquid flavorings, particularly raspberry, strawberry and honey.

Suitable sweeteners include, for example, saccharin sodium, saccharin, cyclamate, acesulfam potassium and taumatin.

Moreover, conventional excipients and/or preservatives effective in the pH range, i.e. preferably sodium benzoate in the case of the active substance meloxicam, may be added to a liquid oral suspension according to the invention.

Because of the three-dimensional siloid structure and the adhesion of the suspended solid particles, there is no need to add any surfactants to improve the wetting qualities. Surfactants may have a negative effect in suspensions since the solubility of the solid in the dispersion medium may be increased in some cases, leading to an unwanted growth in particle size. Moreover, surfactants, particularly ionic surfactants, are frequently allergenic and/or irritant to the mucous membranes.

The invention further relates to a process for producing an orally administered liquid preparation of a pharmaceutically active substance of the NSAID type in the form of a stabilised suspension, characterised in that (i) the solid active substance is ground in order to produce a particle size spectrum in which at least 90% of the particles are smaller than 50 µm, preferably at least 50% of the particles are smaller than 10 µm, but in particular about 90% of the particles are smaller than 10 µm, (ii) the ground active substance is suspended in a physiologically inert dispersion medium in which the solubility of the active substance is very low, (iii) small amounts of highly dispersed silicon dioxide are added to the dispersion medium with the application of high shear forces, (iv) small amounts of hydrophilic polymer soluble in the dispersion medium are added to the dispersion medium and (v) optionally, one or more flavorings, one or more sweeteners, conventional excipients or one or more preservatives may, independently of one another, be added to the dispersion medium, the flavorings preferably being added during the final stage of manufacture owing to their foam breaking properties.

A preferred embodiment of the process according to the invention is characterised in that (i) a particle size spectrum is produced in which about 90% of the particles are smaller than 10 µm, (ii) the ground active substance is suspended in a physiologically acceptable, aqueous buffer system at a pH in the range from 2–4, for example sodium dihydrogen phosphate dihydrate/citric acid monohydrate buffer, glycine/HCl, K-hydrogen phthalate/HCl, citric acid/ phosphate, citrate-phosphate-borate/HCl or Britton-Robinson buffer, mixtures thereof with one another or mixtures thereof with other physiologically acceptable liquids such as glycerol or optionally aqueous solutions of sugar alcohols such as sorbitol, mannitol and xylitol, (iii) with the aid of a mixer by the application of high shear forces, characterised for example by a circumferential rotor speed of 15–35 m/s, preferably 20–30 m/s, 0.1–5.0 wt.-% of highly dispersed silicon dioxide, based on the weight of the suspension ready for use, are added to the dispersion medium, (iv) water soluble cellulose ethers of pharmaceutical grade are added to the dispersion medium as hydrophilic polymers in an amount of from 0.05–2 wt.-%, based on the weight of the suspension ready for use, and (v) one or more flavorings, one or more sweeteners, conventional excipients or one or more preservatives may optionally be added independently of one another to the dispersion medium.

A particularly preferred embodiment of the process according to the invention is characterised in that (i) a particle size spectrum is produced in which about 90% of the particles are smaller than 10 µm, (ii) the ground active substance is suspended in a dispersion medium consisting of mixtures of 30–50% aqueous buffer systems with a pH in the range from 2–4, aqueous sodium dihydrogen phosphate dihydrate/citric acid monohydrate buffer being preferred, 10–20% glycerol, 10–20% xylitol and 20–30% sorbitol or mannitol solution (70% sorbitol or mannitol in water), whilst glycerol and the above-mentioned sugar alcohols may be present in the dispersion medium either individually or in admixture with one another, (iii) 0.5–2.0 wt.-% of highly dispersed silicon dioxide, based on the weight of the suspension ready for use, are added to the dispersion medium with the aid of a mixer by applying high shear forces, characterised for example by a circumferential rotor speed of 20 to 30 m/s, preferably about 25 to 27 m/s, (iv) pharmaceutical grade water-soluble cellulose ethers, preferably hydroxyethyl cellulose, are added to the dispersion medium as hydrophilic polymers, in an amount of from 0.05–0.5 wt.-%, based on the weight of the suspension ready for use, and (v) one or more flavorings, one or more sweeteners, conventional excipients or one or more preservatives may optionally be added to the dispersion medium independently of one another.

In all the above-mentioned embodiments of the process, steps (ii) to (v) are preferably carried out in vacuo since the entry of air affects the density of the suspension to be produced, as a result of floating effects or air absorption on the siloid structure, and inhomogeneities may be produced.

A particularly preferred embodiment of the process according to the invention is characterised in that the active substance is an acid enolcarboxamide, particularly meloxicam.

A third object of the invention is the use of an active substance of the NSAID type, preferably an acid enolcarboxamide, but particularly meloxicam, for preparing a liquid preparation of the active substance in the form of a stabilised suspension with a particle size spectrum wherein at least 90% of the particles are smaller than 50 µm, in a physiologically inert dispersion medium in which the active substance has very low solubility, so that the suspension does not have any noticeable taste, for oral administration, characterised in that the suspension contains a small amount of highly dispersed silicon dioxide for stabilising it by forming a three-dimensional siloid structure, the three-dimensional siloid structure being produced by adding the silicon dioxide to the dispersion medium with the action of high shear forces, and the suspension additionally contains a small amount of hydrophilic polymer soluble in the dispersion medium.

EXAMPLE

The following recipe is for the preparation of 100 ml of a liquid, orally administered suspension of meloxicam according to the invention. The formulation makes it possible to take several doses of 7.5 mg of meloxicam in a volume of 5 ml from a suitably sized glass bottle by pouring into standard plastic measuring spoons. The ingredients which are relevant to the effectiveness and the formation of the siloid structure according to the invention are given quantitatively, whilst all the other ingredients may be present in the formulation in accordance with the information provided above.

In order to protect it from microbial contamination during use (multi-dose container) the preparation must be suitably preserved with a preservative (in this case sodium benzoate) adapted to the pH range of the dispersion medium.

|     | Ingredient | Formulation A g/100 ml (= g/118 g) | Formulation B g/100 ml (= g/118 g) |
| --- | --- | --- | --- |
| (1) | Meloxicam, jet-ground | 0.150 | 1.500 |
| (2) | Silicion dioxide, Highly dispersed | 1.000 | 1.500 |
| (3) | Hydroxyethylcellulose | 0.100 | 0.050 |

Other ingredients are:

70% sorbitol solution (non-crystalline), 85% glycerol, xylitol, sodium dihydrogen phosphate dihydrate, citric acid monohydrate, saccharin sodium crystals, sodium benzoate and raspberry flavoring D 9599 (formulation A) or honey flavoring 203108 (formulation B). The mixture is made up to a final volume of 100 ml, corresponding to 118.000 g, with purified water.

Physical/chemical Properties of the Preparations

|  | Formulation A | Formulation B |
| --- | --- | --- |
| pH: | 3.5–4.5 | 3.5–4.5 |
| Density: | 1.16–1.20 g/ml (20° C.) | 1.16–1.20 g/ml (20° C.) |
| Viscosity: | 40–150 mPas | 60–200 mPas |

Pharmacokinetic Properties of the Preparation

A main objective for developing a liquid oral formulation of meloxicam was the rapid onset of activity on first use. The prerequisite for this is the fastest possible flooding of the drug into the central blood compartment.

In the formulation according to the above Example this is achieved. In a direct comparison between a suspension according to the invention and a capsule containing the same dose, the time for maximum plasma concentration on a single dose of meloxicam is $t_{max}$=2 h (1.5–5 h; suspension) as against $t_{max}$=5 h (2–6 h; capsule).

In the steady state, bioequivalence should be detectable owing to the desired therapeutic equivalents of the suspension according to the invention and a solid oral formulation. This has been shown by direct comparison of a suspension according to the invention with a capsule containing the same dose. In the steady state the maximum plasma levels are at $t_{max\ (ss)}$=5.0 h (5–9 h; suspension) and $t_{max\ (ss)}$=5.0 h (3–7 h; capsule). A graphic representation of the results of the study is shown in FIG. 1.

Method of Preparation

Suspensions according to the invention can be prepared by a multi-stage mixing and homogenising process. The use of shear-intensive homogenising mixers which enable the solid particles of the active substance which are to be suspended and the highly dispersed silicon dioxide to be distributed in the dispersion medium within a very short time is crucial to the production of a homogeneous suspension having the siloid structure described. Different sizes of process mixers from the series "Becomix" (made by Messrs. A. Berents GmbH & Co. KG, Henleinstr. 19, D-28816 Stuhr) have proved particularly suitable for this purpose and will produce suspensions according to the invention in batch sizes ranging from 2.5 to 1,000 kg. These mixers incorporate fast rotating homogenizers working on the rotor-stator principle which ensure optimum mixing and production of the three-dimensional siloid structure described above. Sufficiently high shear forces are generated, for example, at a circumferential rotor speed of 20 to 30 m/s, preferably about 25 to 27 m/s. With the mixers Becomix RW 60/RW 1000, circumferential rotor speeds of about 26 m/s are used for about 10–15 minutes to introduce the highly dispersed silicon dioxide into the dispersing agent.

Step 1 (Premix)

The active substance and the highly dispersed silicon dioxide are homogeneously premixed in a suitable container (e.g. VA container). This premixing is necessary in order to achieve better wetting properties of the pharmaceutical substance and lump-free distribution in the suspension.

Step 2 (Polymer Solution)

The majority of the water is placed in a suitable batch container (e.g. Becomix mixer) and the HEC is sucked in with stirring, homogenization and in vacuo and then the mixture is stirred for about 10 minutes in vacuo. The HEC is allowed to swell for about 30 min. at room temperature (RT) before heating to about 80° C. in vacuo and maintaining for about 1 hours at this temperature and cooling to RT again.

Step 3 (Sodium Benzoate Solution)

A small amount of the water is placed in a suitable batch container (e.g. VA container) and the sodium benzoate is dissolved therein with stirring.

Step 4 (Final Mixing)

The sodium benzoate solution (see above) and the other ingredients of the composition with the exception of the flavoring are added to the polymer solution (sucked in under vacuum). The mixture is then homogenised. The mixture of active substance and silicon dioxide is then added in vacuo, with stirring and homogenization and the mixture is homogenised for a further 10 minutes in vacuo. The high shear forces described are characterised, for example, in that the mixture of active substance and silicon dioxide in a 1000 kg batch is sucked into the circulation in a mixer of the Becomix RW 1000 type at a rotor speed of about 3500 rpm (corresponding to a circumferential speed of about 26 m/s) and then homogenised for 10 minutes. Finally, the flavoring is added in vacuo, with stirring and homogenization. This method makes use of the foam-breaking properties of the flavoring, which shortens the subsequent process of de-aerating the suspension (vacuum). The suspension can be transferred from the mixer into bulk containers under pressure.

What is claimed is:

1. A pharmaceutical composition of matter which is an orally administered suspension comprising particles of a non-steroidal anti-inflammtory active substance selected from the acid enolcarboxamides (oxicams), and pharmaceutically acceptable salts thereof, having a suspendable particle size spectrum in which at least 90% of the particles are smaller than 50 $\mu$m, a physiologically inert dispersion medium in which the particles of active substance are suspended and in which dispersion medium the active substance has a solubility of less than 500 $\mu$g/ml, about 0.1 to about 5% by weight of highly dispersed silicon dioxide having a specific surface area of at least 50 $m^2$/g, forming a three-dimensional siloid structure produced by adding the silicon dioxide to the dispersion medium with the action of shear forces characterised by a circumferential rotor speed of about 15 to 35 m/s, and about 0.05 to about 2% by weight of a hydrophilic polymer, which polymer is soluble in the dispersion medium.

2. The pharmaceutical composition of matter as recited in claim 1 wherein the active substance is selected from the group consisting of piroxicam, tenoxicam, lomoxicam, meloxicam and the pharmaceutically acceptable salts thereof.

3. The pharmaceutical composition of matter as recited in claim 1 wherein the highly dispersed silicon dioxide is present in an amount of from about 0.5% to about 2% by weight.

4. The pharmaceutical composition of matter as recited in claim 1 wherein the hydrophilic polymer is a pharmaceutical-grade water soluble cellulose ether.

5. The pharmaceutical composition of matter as recited in claim 4 wherein the cellulose ether is present in an amount of from about 0.05% to about 0.5% by weight.

6. The pharmaceutical composition of matter as recited in claim 4 wherein the cellulose ether is selected from the group consisting of hydroxyethyl cellulose, hydroxypropyl cellulose and hydroxypropyl methyl cellulose.

7. The pharmaceutical composition of matter as recited in claim 1 wherein at least about 50% of the particles of active substance are smaller than about 10 $\mu$m.

8. The pharmaceutical composition of matter as recited in claim 1 wherein the active substance is meloxicam and the dispersion medium is an aqueous buffer system with a pH in the range from about 2–4.

9. The pharmaceutical composition of matter as recited in claim 8 wherein the dispersion medium is a mixture of a physiologically acceptable aqueous buffer system with glycerol or with an aqueous solution of one or more sugar alcohols selected from the group consisting of xylitol, sorbitol and mannitol.

10. The pharmaceutical composition of matter as recited in claim 8 wherein the dispersion medium is a buffer system from the group consisting of (a) sodium dihydrogen phosphate dihydrate/citric acid monohydrate,
(b) glycin/HCl,
(c) Na-citrate/HCl,
(d) K-hydrogen phthalate/HCl,
(e) citric acid/phosphate,
(f) citrate-phosphate-borate/HCl and
(g) Britton-Robinson buffer.

11. The pharmaceutical composition of matter as recited in claim 9 wherein the dispersion medium is a mixture of about 30 to about 50% aqueous sodium dihydrogen phosphate dihydrate/citric acid mono-hydrate buffer, about 10 to about 20% glycerol, about 10 to about 20% xylitol and about 20 to about 30% sorbitol or mannitol solution, the sorbitol or mannitol solution being an about 70% aqueous solution.

12. The pharmaceutical composition of matter as recited in claim 8 wherein the composition of matter comprises about 0.050 to about 3.000 g of meloxicam in about 118 g of pharmaceutical composition of matter.

13. The pharmaceutical composition of matter as recited in claim 1 further comprising a flavoring agent, a sweetener, a preservative or a mixture of such.

* * * * *

UNITED STATES PATENT AND TRADEMARK OFFICE
CERTIFICATE OF CORRECTION

PATENT NO.   : 6,184,220 B1
DATED        : February 6, 2001
INVENTOR(S)  : Dietrich Turck and Veit Schmelmer It is certified that error appears in the above-identified patent and that said Letters Patent is hereby corrected as shown below:

Column 5,
Line 1, "acetylsalicyclic" should read -- acetylsalicylic --.

Column 9,
Line 35, "Silicion dioxide" should read -- Silicon dioxide --

Column 11,
Line 17, "anti-inflammtory" should read -- anti-inflammatory --

Signed and Sealed this

Fourth Day of June, 2002

Attest:

Attesting Officer

JAMES E. ROGAN
Director of the United States Patent and Trademark Office